(12) United States Patent
Chen et al.

(10) Patent No.: US 7,741,094 B2
(45) Date of Patent: Jun. 22, 2010

(54) PROTEIN HAVING PROLYL OLIGOPEPTIDASE ACTIVITY, AND COMPOSITION CONTAINING THE SAME

(75) Inventors: Jen-Tao Chen, Hsinchu (TW); Mei-Li Chao, Hsinchu (TW); Chiou-Yen Wen, Hsinchu (TW); Wen-Shen Chu, Hsinchu (TW)

(73) Assignee: Food Industry Research & Development Institute, Hsinchu (TW)

( * ) Notice: Subject to any disclaimer, the term of this patent is extended or adjusted under 35 U.S.C. 154(b) by 6 days.

(21) Appl. No.: 12/081,984

(22) Filed: Apr. 24, 2008

(65) Prior Publication Data

US 2009/0269327 A1    Oct. 29, 2009

(51) Int. Cl.
*C12N 9/48* (2006.01)
(52) U.S. Cl. ...................................... 435/212
(58) Field of Classification Search ........................ None
See application file for complete search history.

(56) References Cited

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Marti et al, Prolyl endopeptidase-mediated destruction of T cell epitopes in whole gluten: chemical and immunological characterization. J Pharmacol Exp Ther. Jan. 2005;312(1):19-26. Epub Sep. 9, 2004.*
Piper et al, Effect of prolyl endopeptidase on digestive-resistant gliadin peptides in vivo. J Pharmacol Exp Ther. Oct. 2004;311(1):213-9. Epub May 13, 2004.*
Gass et al, Fermentation, purification, formulation, and pharmacological evaluation of a prolyl endopeptidase from *Myxococcus xanthus*: implications for Celiac Sprue therapy. Biotechnol Bioeng. Dec. 20, 2005;92(6):674-84.*
Matysiak-Budnik et al, Limited efficiency of prolyl-endopeptidase in the detoxification of gliadin peptides in celiac disease. Gastroenterology. Sep. 2005;129(3):786-96.*
Pyle et al, Effect of Pretreatment of Food Gluten With Prolyl Endopeptidase on Gluten-Induced Malabsorption in Celiac Sprue Clinical Gastroenterology and Hepatology, (2005) vol. 3, Issue 7, pp. 687-694.*

* cited by examiner

*Primary Examiner*—Sheridan Swope
(74) *Attorney, Agent, or Firm*—Frenkel & Associates, PC

(57) ABSTRACT

A protein of amino acid sequence SEQ ID NO:6 isolated from *Coprinus clastophyllus*. The protein is stable at 30 to 37 degrees centigrade and has an optimal prolyl oligopeptidase activity at about 45 degree centigrade and at about pH 7. The present invention also relates to a medicament comprising such protein for treating celiac disease caused by proline abundant gluten.

4 Claims, 4 Drawing Sheets

SEQUENCE LISTING

<160> NUMBER OF SEQ ID NOS: 11

<210> SEQ ID NO 1
<211> LENGTH: 20
<212> TYPE: DNA
<213> ORGANISM: artificial
<220> FEATURE:
<223> OTHER INFORMATION: synthesized

<400> SEQUENCE: 1
tacggcggmt tcascatctc                                                    20

<210> SEQ ID NO 2
<211> LENGTH: 20
<212> TYPE: DNA
<213> ORGANISM: artificial
<220> FEATURE:
<223> OTHER INFORMATION: synthesized

<400> SEQUENCE: 2
tgccaytcyt cwccraactc                                                    20

<210> SEQ ID NO 3
<211> LENGTH: 20
<212> TYPE: DNA
<213> ORGANISM: artificial
<220> FEATURE:
<223> OTHER INFORMATION: synthesized

<400> SEQUENCE: 3
tacggcggat tcagcatctc                                                    20

<210> SEQ ID NO 4
<211> LENGTH: 20
<212> TYPE: DNA
<213> ORGANISM: artificial
<220> FEATURE:
<223> OTHER INFORMATION: synthesized

<400> SEQUENCE: 4
tgccactcct caccaaactc                                                    20

<210> SEQ ID NO 5
<211> LENGTH: 2508
<212> TYPE: DNA
<213> ORGANISM: Coprinus clastophyllus
<220> FEATURE:
<221> NAME/KEY: CDS
<222> LOCATION: (65)..(2284)

<400> SEQUENCE: 5
ccacagttct ctctgtagac gcgtttggcc atccataact cgtcctcagc gtttctcgac        60 agct atg gtg acc aaa acc tgg gtt cct gac acg tat ccg caa gcc cgg       109
     Met Val Thr Lys Thr Trp Val Pro Asp Thr Tyr Pro Gln Ala Arg
       1               5                  10                  15 cgc tgc gac cac gtt gat acg tac acg agc gcc aaa cat ggc gag gtc        157
Arg Cys Asp His Val Asp Thr Tyr Thr Ser Ala Lys His Gly Glu Val
                 20                  25                  30 aag gtc gcg gac cct tat agg tgg atg gag gag tat acg gac gag acg        205
Lys Val Ala Asp Pro Tyr Arg Trp Met Glu Glu Tyr Thr Asp Glu Thr
             35                  40                  45

| | | |
|---|---|---|
| gac aaa tgg acg tct gct cag gaa gcg tat aca cgc gcg tat atc gat<br>Asp Lys Trp Thr Ser Ala Gln Glu Ala Tyr Thr Arg Ala Tyr Ile Asp<br>50 55 60 | | 253 |
| aaa tac cct cat cgg cag cgg ttg gaa gat gcg ttc atg gcc agt ctg<br>Lys Tyr Pro His Arg Gln Arg Leu Glu Asp Ala Phe Met Ala Ser Leu<br>65 70 75 | | 301 |
| gac tat gcc agg gct ggt gca cca gtc aag agt gac aag aaa cgg tgg<br>Asp Tyr Ala Arg Ala Gly Ala Pro Val Lys Ser Asp Lys Lys Arg Trp<br>80 85 90 95 | | 349 |
| tac tgg tcc tat aac agc gga ttg cag cct cag aac gtt tac tac cgg<br>Tyr Trp Ser Tyr Asn Ser Gly Leu Gln Pro Gln Asn Val Tyr Tyr Arg<br>100 105 110 | | 397 |
| tcg agg gac gga caa cta cct gat agg tcc aaa ggg ctc gac aat gga<br>Ser Arg Asp Gly Gln Leu Pro Asp Arg Ser Lys Gly Leu Asp Asn Gly<br>115 120 125 | | 445 |
| gag gtc ttc atg gat atg aac ctc ctt tcg gag gac ggg aca gca gcc<br>Glu Val Phe Met Asp Met Asn Leu Leu Ser Glu Asp Gly Thr Ala Ala<br>130 135 140 | | 493 |
| atc agt gtc cac gcg ttc tct gac aat gga gag tac tac gcc tat ggt<br>Ile Ser Val His Ala Phe Ser Asp Asn Gly Glu Tyr Tyr Ala Tyr Gly<br>145 150 155 | | 541 |
| gta tca tac tcc gga agc gac ttc acc acc gtc tac att cgg cgg aca<br>Val Ser Tyr Ser Gly Ser Asp Phe Thr Thr Val Tyr Ile Arg Arg Thr<br>160 165 170 175 | | 589 |
| gac tct ccg cta gct tca aag gaa cag gcc gag aaa gac acc ggt cgt<br>Asp Ser Pro Leu Ala Ser Lys Glu Gln Ala Glu Lys Asp Thr Gly Arg<br>180 185 190 | | 637 |
| cta ccg gac gtt ctc aac tac gtt aaa ttt tcc tct ctt cgc tgg acg<br>Leu Pro Asp Val Leu Asn Tyr Val Lys Phe Ser Ser Leu Arg Trp Thr<br>195 200 205 | | 685 |
| cct gac tcg aag ggc ttc ttc tac cag aga tac ccg gac cac aat gga<br>Pro Asp Ser Lys Gly Phe Phe Tyr Gln Arg Tyr Pro Asp His Asn Gly<br>210 215 220 | | 733 |
| aac acc ggc tct gat aag cct agc gac tct gga att gag acc aga ggc<br>Asn Thr Gly Ser Asp Lys Pro Ser Asp Ser Gly Ile Glu Thr Arg Gly<br>225 230 235 | | 781 |
| gat aag gac gcc atg ctt tat tat cat cgc gtt aac act cct caa tct<br>Asp Lys Asp Ala Met Leu Tyr Tyr His Arg Val Asn Thr Pro Gln Ser<br>240 245 250 255 | | 829 |
| gag gat atc ctc gta tac tac gac aag acg aaa ccc gac tgg atg tac<br>Glu Asp Ile Leu Val Tyr Tyr Asp Lys Thr Lys Pro Asp Trp Met Tyr<br>260 265 270 | | 877 |
| ggc atc gat gtt act gac gat gac aag tac gtc gtc atg agc gtt gtt<br>Gly Ile Asp Val Thr Asp Asp Asp Lys Tyr Val Val Met Ser Val Val<br>275 280 285 | | 925 |
| cag gat act tcg agg aaa aat ctg ctt tgg ata gca gag ctc acg gac<br>Gln Asp Thr Ser Arg Lys Asn Leu Leu Trp Ile Ala Glu Leu Thr Asp<br>290 295 300 | | 973 |
| gac ttc atc gag aag ggc ttc aaa tgg aac agg gtc atg gac aag ttt<br>Asp Phe Ile Glu Lys Gly Phe Lys Trp Asn Arg Val Met Asp Lys Phe<br>305 310 315 | | 1021 |
| gac gct gaa tat gaa tat atc aag aat gag ggt cct gtc ttt gtc ctc<br>Asp Ala Glu Tyr Glu Tyr Ile Lys Asn Glu Gly Pro Val Phe Val Leu<br>320 325 330 335 | | 1069 |
| cga acc aac gag aat gcg cca aaa tat aag gtg gtc acg gtg gac gtg<br>Arg Thr Asn Glu Asn Ala Pro Lys Tyr Lys Val Val Thr Val Asp Val<br>340 345 350 | | 1117 |
| tcc aag gac aat gaa gtc aaa ccg ttc atc cct gag agt gac ggg ttc<br>Ser Lys Asp Asn Glu Val Lys Pro Phe Ile Pro Glu Ser Asp Gly Phe<br>355 360 365 | | 1165 |

```
ttg gag agc atc tac gcc gtc aac aag ggg aat aac ttt gtt gtc act   1213
Leu Glu Ser Ile Tyr Ala Val Asn Lys Gly Asn Asn Phe Val Val Thr
        370                 375                 380 tac aag cgg aat gtc aaa gat gag att tat gtc tac tcg aaa gag ggc   1261
Tyr Lys Arg Asn Val Lys Asp Glu Ile Tyr Val Tyr Ser Lys Glu Gly
385                 390                 395 aaa gaa ctc gaa cgg ctt gtt cct gat ttt atc ggt tca gct tca gta   1309
Lys Glu Leu Glu Arg Leu Val Pro Asp Phe Ile Gly Ser Ala Ser Val
400                 405                 410                 415 act gcg aga tgg gaa gat acc tgg ttc ttc atc aac tgc agc ggg ttc   1357
Thr Ala Arg Trp Glu Asp Thr Trp Phe Phe Ile Asn Cys Ser Gly Phe
                420                 425                 430 aca acg ccc ggc acg att ggg cga tac gac ttt aca gcg cct gaa ggg   1405
Thr Thr Pro Gly Thr Ile Gly Arg Tyr Asp Phe Thr Ala Pro Glu Gly
            435                 440                 445 cag cgg tgg agt acc tac cac caa act cag gtg aat ggt ctg aac ccg   1453
Gln Arg Trp Ser Thr Tyr His Gln Thr Gln Val Asn Gly Leu Asn Pro
        450                 455                 460 gaa gag ttt gaa gca aga cag gac tgg tac gag agc aag gac ggg acc   1501
Glu Glu Phe Glu Ala Arg Gln Asp Trp Tyr Glu Ser Lys Asp Gly Thr
465                 470                 475 aag att cct atg ttc atc gtt cgt cac aag tcg acg cca ttt gat ggg   1549
Lys Ile Pro Met Phe Ile Val Arg His Lys Ser Thr Pro Phe Asp Gly
480                 485                 490                 495 act gct cca gca gtc caa tac ggt tat ggc ggt ttc agc atc tca atc   1597
Thr Ala Pro Ala Val Gln Tyr Gly Tyr Gly Gly Phe Ser Ile Ser Ile
                500                 505                 510 aac ccc ttc ttt agc ccg acc atc ctc act ttc ttg aag aca tac gga   1645
Asn Pro Phe Phe Ser Pro Thr Ile Leu Thr Phe Leu Lys Thr Tyr Gly
            515                 520                 525 gca gtc tac gct gtt gcc aat atc aga ggg gga ggc gag ttt gga gag   1693
Ala Val Tyr Ala Val Ala Asn Ile Arg Gly Gly Gly Glu Phe Gly Glu
        530                 535                 540 gag tgg cat gaa aat ggt atg agg gaa aag aag cac aat tgc ttt gac   1741
Glu Trp His Glu Asn Gly Met Arg Glu Lys Lys His Asn Cys Phe Asp
545                 550                 555 gac ttc atc gct gga gcc gag tat ctt gta aag agc aag tat gct gct   1789
Asp Phe Ile Ala Gly Ala Glu Tyr Leu Val Lys Ser Lys Tyr Ala Ala
560                 565                 570                 575 cca gga aaa gtc acc atc aat ggc ggg tcg aat gga ggt ctc ctt gtt   1837
Pro Gly Lys Val Thr Ile Asn Gly Gly Ser Asn Gly Gly Leu Leu Val
                580                 585                 590 tct gct tgc gtg aat cga gca ccc gaa ggc acg ttc ggt gct gca att   1885
Ser Ala Cys Val Asn Arg Ala Pro Glu Gly Thr Phe Gly Ala Ala Ile
            595                 600                 605 gcg gaa gtt ggt gta cat gat ttg ctt cga ttc cat aaa ttc aca atc   1933
Ala Glu Val Gly Val His Asp Leu Leu Arg Phe His Lys Phe Thr Ile
        610                 615                 620 gga cga gcc tgg ata agc gac tac ggt gac ccg gac gat cct aaa gac   1981
Gly Arg Ala Trp Ile Ser Asp Tyr Gly Asp Pro Asp Asp Pro Lys Asp
625                 630                 635 ttt gac ttc atc tat cct atc tcg cca ctg cag aat gtc tcg ccc aca   2029
Phe Asp Phe Ile Tyr Pro Ile Ser Pro Leu Gln Asn Val Ser Pro Thr
640                 645                 650                 655 aag gtt cta ccg ccc tac atg ctc tca act gct gat cac gac gac cgt   2077
Lys Val Leu Pro Pro Tyr Met Leu Ser Thr Ala Asp His Asp Asp Arg
                660                 665                 670 gtc gta ccc agt cac tcg ttc aag atg gca gct act cta caa cat ctg   2125
Val Val Pro Ser His Ser Phe Lys Met Ala Ala Thr Leu Gln His Leu
            675                 680                 685
```

```
cga gcg aac aac cct agt cct att ctc ctg agg gtg gat aag aag gct      2173
Arg Ala Asn Asn Pro Ser Pro Ile Leu Leu Arg Val Asp Lys Lys Ala
        690                 695                 700 gga cat ggc gcc ggg aag tcg act aag aag agg gtc gaa gag tcg gcg      2221
Gly His Gly Ala Gly Lys Ser Thr Lys Lys Arg Val Glu Glu Ser Ala
705                 710                 715 gat aag tgg agt ttt gtt gcg cag gct ttg ggc ttg gag tgg aaa gat      2269
Asp Lys Trp Ser Phe Val Ala Gln Ala Leu Gly Leu Glu Trp Lys Asp
720                 725                 730                 735 aaa gct aca ctc tag gtccctggtc tctgatgtct tgggattgcg gttgggtatc      2324
Lys Ala Thr Leu tcattgaggc gatattcggg ctttggacat ggcttccgca tggacatctg ttatacacga    2384
tttgctatcg ggttgtttat actgtagcta ctctactaat tggatgctca gcttggtgca    2444
ggcgttgctg gtgcaatgtc tgtttttaga aaaaaaaaaa aaaaaaaaaa aaaaaaaaaa    2504
aaaa                                                                 2508
```

<210> SEQ ID NO 6
<211> LENGTH: 739
<212> TYPE: PRT
<213> ORGANISM: Coprinus clastophyllus

<400> SEQUENCE: 6

```
Met Val Thr Lys Thr Trp Val Pro Asp Thr Tyr Pro Gln Ala Arg Arg
1               5                   10                  15

Cys Asp His Val Asp Thr Tyr Thr Ser Ala Lys His Gly Glu Val Lys
            20                  25                  30

Val Ala Asp Pro Tyr Arg Trp Met Glu Glu Tyr Thr Asp Glu Thr Asp
        35                  40                  45

Lys Trp Thr Ser Ala Gln Glu Ala Tyr Thr Arg Ala Tyr Ile Asp Lys
    50                  55                  60

Tyr Pro His Arg Gln Arg Leu Glu Asp Ala Phe Met Ala Ser Leu Asp
65                  70                  75                  80

Tyr Ala Arg Ala Gly Ala Pro Val Lys Ser Asp Lys Lys Arg Trp Tyr
                85                  90                  95

Trp Ser Tyr Asn Ser Gly Leu Gln Pro Gln Asn Val Tyr Tyr Arg Ser
            100                 105                 110

Arg Asp Gly Gln Leu Pro Asp Arg Ser Lys Gly Leu Asp Asn Gly Glu
        115                 120                 125

Val Phe Met Asp Met Asn Leu Leu Ser Glu Asp Gly Thr Ala Ala Ile
    130                 135                 140

Ser Val His Ala Phe Ser Asp Asn Gly Glu Tyr Tyr Ala Tyr Gly Val
145                 150                 155                 160

Ser Tyr Ser Gly Ser Asp Phe Thr Thr Val Tyr Ile Arg Arg Thr Asp
                165                 170                 175

Ser Pro Leu Ala Ser Lys Glu Gln Ala Glu Lys Asp Thr Gly Arg Leu
            180                 185                 190

Pro Asp Val Leu Asn Tyr Val Lys Phe Ser Ser Leu Arg Trp Thr Pro
        195                 200                 205

Asp Ser Lys Gly Phe Phe Tyr Gln Arg Tyr Pro Asp His Asn Gly Asn
    210                 215                 220

Thr Gly Ser Asp Lys Pro Ser Asp Ser Gly Ile Glu Thr Arg Gly Asp
225                 230                 235                 240

Lys Asp Ala Met Leu Tyr Tyr His Arg Val Asn Thr Pro Gln Ser Glu
                245                 250                 255
```

-continued

```
Asp Ile Leu Val Tyr Tyr Asp Lys Thr Lys Pro Asp Trp Met Tyr Gly
            260                 265                 270

Ile Asp Val Thr Asp Asp Lys Tyr Val Val Met Ser Val Val Gln
        275                 280                 285

Asp Thr Ser Arg Lys Asn Leu Leu Trp Ile Ala Glu Leu Thr Asp Asp
    290                 295                 300

Phe Ile Glu Lys Gly Phe Lys Trp Asn Arg Val Met Asp Lys Phe Asp
305                 310                 315                 320

Ala Glu Tyr Glu Tyr Ile Lys Asn Glu Gly Pro Val Phe Val Leu Arg
                325                 330                 335

Thr Asn Glu Asn Ala Pro Lys Tyr Lys Val Val Thr Val Asp Val Ser
            340                 345                 350

Lys Asp Asn Glu Val Lys Pro Phe Ile Pro Glu Ser Asp Gly Phe Leu
        355                 360                 365

Glu Ser Ile Tyr Ala Val Asn Lys Gly Asn Asn Phe Val Val Thr Tyr
    370                 375                 380

Lys Arg Asn Val Lys Asp Glu Ile Tyr Val Tyr Ser Lys Glu Gly Lys
385                 390                 395                 400

Glu Leu Glu Arg Leu Val Pro Asp Phe Ile Gly Ser Ala Ser Val Thr
                405                 410                 415

Ala Arg Trp Glu Asp Thr Trp Phe Phe Ile Asn Cys Ser Gly Phe Thr
            420                 425                 430

Thr Pro Gly Thr Ile Gly Arg Tyr Asp Phe Thr Ala Pro Glu Gly Gln
        435                 440                 445

Arg Trp Ser Thr Tyr His Gln Thr Gln Val Asn Gly Leu Asn Pro Glu
    450                 455                 460

Glu Phe Glu Ala Arg Gln Asp Trp Tyr Glu Ser Lys Asp Gly Thr Lys
465                 470                 475                 480

Ile Pro Met Phe Ile Val Arg His Lys Ser Thr Pro Phe Asp Gly Thr
                485                 490                 495

Ala Pro Ala Val Gln Tyr Gly Tyr Gly Gly Phe Ser Ile Ser Ile Asn
            500                 505                 510

Pro Phe Phe Ser Pro Thr Ile Leu Thr Phe Leu Lys Thr Tyr Gly Ala
        515                 520                 525

Val Tyr Ala Val Ala Asn Ile Arg Gly Gly Gly Glu Phe Gly Glu Glu
    530                 535                 540

Trp His Glu Asn Gly Met Arg Glu Lys Lys His Asn Cys Phe Asp Asp
545                 550                 555                 560

Phe Ile Ala Gly Ala Glu Tyr Leu Val Lys Ser Lys Tyr Ala Ala Pro
                565                 570                 575

Gly Lys Val Thr Ile Asn Gly Gly Ser Asn Gly Gly Leu Leu Val Ser
            580                 585                 590

Ala Cys Val Asn Arg Ala Pro Glu Gly Thr Phe Gly Ala Ala Ile Ala
        595                 600                 605

Glu Val Gly Val His Asp Leu Leu Arg Phe His Lys Phe Thr Ile Gly
    610                 615                 620

Arg Ala Trp Ile Ser Asp Tyr Gly Asp Pro Asp Asp Pro Lys Asp Phe
625                 630                 635                 640

Asp Phe Ile Tyr Pro Ile Ser Pro Leu Gln Asn Val Ser Pro Thr Lys
                645                 650                 655

Val Leu Pro Pro Tyr Met Leu Ser Thr Ala Asp His Asp Asp Arg Val
            660                 665                 670
```

-continued

```
Val Pro Ser His Ser Phe Lys Met Ala Ala Thr Leu Gln His Leu Arg
        675                 680                 685

Ala Asn Asn Pro Ser Pro Ile Leu Leu Arg Val Asp Lys Lys Ala Gly
    690                 695                 700

His Gly Ala Gly Lys Ser Thr Lys Lys Arg Val Glu Glu Ser Ala Asp
705                 710                 715                 720

Lys Trp Ser Phe Val Ala Gln Ala Leu Gly Leu Glu Trp Lys Asp Lys
                725                 730                 735

Ala Thr Leu

<210> SEQ ID NO 7
<211> LENGTH: 20
<212> TYPE: DNA
<213> ORGANISM: artificial
<220> FEATURE:
<223> OTHER INFORMATION: synthesized

<400> SEQUENCE: 7
atggtgacca aaacctgggt                                                    20

<210> SEQ ID NO 8
<211> LENGTH: 22
<212> TYPE: DNA
<213> ORGANISM: artificial
<220> FEATURE:
<223> OTHER INFORMATION: synthesized

<400> SEQUENCE: 8
ctagagtgta gctttatctt tc                                                 22

<210> SEQ ID NO 9
<211> LENGTH: 2289
<212> TYPE: DNA
<213> ORGANISM: Coprinus clastophyllus
<220> FEATURE:
<221> NAME/KEY: CDS
<222> LOCATION: (1)..(2289)
<223> OTHER INFORMATION: The 'Xaa' at location 171 stands for Tyr.

<400> SEQUENCE: 9 atg gtg acc aaa acc tgg gtt cct gac acg tat ccg caa gcc cgg cgc       48
Met Val Thr Lys Thr Trp Val Pro Asp Thr Tyr Pro Gln Ala Arg Arg
1               5                   10                  15 tgc gac cac gtt gat acg tac acg agc gcc aaa cat ggc gag gtc aag       96
Cys Asp His Val Asp Thr Tyr Thr Ser Ala Lys His Gly Glu Val Lys
            20                  25                  30 gtc gcg gac cct tat agg tgg atg gag gag tat acg gac gag acg gac      144
Val Ala Asp Pro Tyr Arg Trp Met Glu Glu Tyr Thr Asp Glu Thr Asp
        35                  40                  45 aaa tgg acg tct gct cag gaa gcg tat aca cgc gcg tat atc gat aaa      192
Lys Trp Thr Ser Ala Gln Glu Ala Tyr Thr Arg Ala Tyr Ile Asp Lys
    50                  55                  60 tac cct cat cgg cag cgg ttg gaa gat gcg ttc atg gcc agt ctg gac      240
Tyr Pro His Arg Gln Arg Leu Glu Asp Ala Phe Met Ala Ser Leu Asp
65                  70                  75                  80 tat gcc agg gct ggt gca cca gtc aag agt gac aag aaa cgg tgg tac      288
Tyr Ala Arg Ala Gly Ala Pro Val Lys Ser Asp Lys Lys Arg Trp Tyr
                85                  90                  95 tgg tcc tat aac agc gga ttg cag cct cag aac gtt tac tac cgg tcg      336
Trp Ser Tyr Asn Ser Gly Leu Gln Pro Gln Asn Val Tyr Tyr Arg Ser
            100                 105                 110
```

-continued

| | |
|---|---|
| agg gac gga caa cta cct gat agg tcc aaa ggg ctc gac aat gga gag<br>Arg Asp Gly Gln Leu Pro Asp Arg Ser Lys Gly Leu Asp Asn Gly Glu<br>               115                    120                   125 | 384 |
| gtc ttc atg gat atg aac ctc ctt tcg gag gac ggg aca gca gcc atc<br>Val Phe Met Asp Met Asn Leu Leu Ser Glu Asp Gly Thr Ala Ala Ile<br>130                          135                    140 | 432 |
| agt gtc cac gcg ttc tct gac aat gga gag tac tac gcc tat ggt gta<br>Ser Val His Ala Phe Ser Asp Asn Gly Glu Tyr Tyr Ala Tyr Gly Val<br>145                          150                    155                   160 | 480 |
| tca tac tcc gga agc gac ttc acc acc gtc tam att cgg cgg aca gac<br>Ser Tyr Ser Gly Ser Asp Phe Thr Thr Val Xaa Ile Arg Arg Thr Asp<br>               165                    170                    175 | 528 |
| tct ccg cta gct tca aag gaa cag gcc gag aaa gac acc ggt cgt cta<br>Ser Pro Leu Ala Ser Lys Glu Gln Ala Glu Lys Asp Thr Gly Arg Leu<br>               180                    185                    190 | 576 |
| ccg gac gtt ctc aac tac gtt aaa ttt tcc tct ctt cgc tgg acg cct<br>Pro Asp Val Leu Asn Tyr Val Lys Phe Ser Ser Leu Arg Trp Thr Pro<br>               195                    200                    205 | 624 |
| gac tcg aag ggc ttc ttc tac cag aga tac ccg gac cac aat gga aac<br>Asp Ser Lys Gly Phe Phe Tyr Gln Arg Tyr Pro Asp His Asn Gly Asn<br>          210                    215                    220 | 672 |
| acc ggc tct gat aag cct agc gac tct gga att gag acc aga ggc gat<br>Thr Gly Ser Asp Lys Pro Ser Asp Ser Gly Ile Glu Thr Arg Gly Asp<br>225                        230                    235                   240 | 720 |
| aag gac gcc atg ctt tat tat cat cgc gtt aac act cct caa tct gag<br>Lys Asp Ala Met Leu Tyr Tyr His Arg Val Asn Thr Pro Gln Ser Glu<br>                        245                    250                    255 | 768 |
| gat atc ctc gta tac tac gac aag acg aaa ccc gac tgg atg tac ggc<br>Asp Ile Leu Val Tyr Tyr Asp Lys Thr Lys Pro Asp Trp Met Tyr Gly<br>                        260                    265                    270 | 816 |
| atc gat gtt act gac gat gac aag tac gtc gtc atg agc gtt gtt cag<br>Ile Asp Val Thr Asp Asp Asp Lys Tyr Val Val Met Ser Val Val Gln<br>                        275                    280                    285 | 864 |
| gat act tcg agg aaa aat ctg ctt tgg ata gca gag ctc acg gac gac<br>Asp Thr Ser Arg Lys Asn Leu Leu Trp Ile Ala Glu Leu Thr Asp Asp<br>          290                    295                    300 | 912 |
| ttc atc gag aag ggc ttc aaa tgg aac agg gtc atg gac aag ttt gac<br>Phe Ile Glu Lys Gly Phe Lys Trp Asn Arg Val Met Asp Lys Phe Asp<br>305                        310                    315                   320 | 960 |
| gct gaa tat gaa tat atc aag aat gag ggt cct gtc ttt gtc ctc cga<br>Ala Glu Tyr Glu Tyr Ile Lys Asn Glu Gly Pro Val Phe Val Leu Arg<br>                        325                    330                    335 | 1008 |
| acc aac gag aat gcg cca aaa tat aag gtg gtc acg gtg gac gtg tcc<br>Thr Asn Glu Asn Ala Pro Lys Tyr Lys Val Val Thr Val Asp Val Ser<br>                      340                    345                    350 | 1056 |
| aag gac aat gaa gtc aaa ccg ttc atc cct gag agt gac ggg ttc ttg<br>Lys Asp Asn Glu Val Lys Pro Phe Ile Pro Glu Ser Asp Gly Phe Leu<br>          355                    360                    365 | 1104 |
| gag agc atc tac gcc gtc aac aag ggg aat aac ttt gtt gtc act tac<br>Glu Ser Ile Tyr Ala Val Asn Lys Gly Asn Asn Phe Val Val Thr Tyr<br>          370                    375                    380 | 1152 |
| aag cgg aat gtc aaa gat gag att tat gtc tac tcg aaa gag ggc aaa<br>Lys Arg Asn Val Lys Asp Glu Ile Tyr Val Tyr Ser Lys Glu Gly Lys<br>385                        390                    395                   400 | 1200 |
| gaa ctc gaa cgg ctt gtt cct gat ttt atc ggt tca gct tca gta act<br>Glu Leu Glu Arg Leu Val Pro Asp Phe Ile Gly Ser Ala Ser Val Thr<br>                        405                    410                    415 | 1248 |
| gcg aga tgg gaa gat acc tgg ttc ttc atc aac tgc agc ggg ttc aca<br>Ala Arg Trp Glu Asp Thr Trp Phe Phe Ile Asn Cys Ser Gly Phe Thr<br>                        420                    425                    430 | 1296 |

```
acg ccc ggc acg att ggg cga tac gac ttt aca gcg cct gaa ggg cag      1344
Thr Pro Gly Thr Ile Gly Arg Tyr Asp Phe Thr Ala Pro Glu Gly Gln
        435                 440                 445 cgg tgg agt acc tac cac caa act cag gtg aat ggt ctg aac ccg gaa      1392
Arg Trp Ser Thr Tyr His Gln Thr Gln Val Asn Gly Leu Asn Pro Glu
450                 455                 460 gag ttt gaa gca aga cag gac tgg tac gag agc aag gac ggg acc aag      1440
Glu Phe Glu Ala Arg Gln Asp Trp Tyr Glu Ser Lys Asp Gly Thr Lys
465                 470                 475                 480 att cct atg ttc atc gtt cgt cac aag tcg acg cca ttt gat ggg act      1488
Ile Pro Met Phe Ile Val Arg His Lys Ser Thr Pro Phe Asp Gly Thr
                485                 490                 495 gct cca gca gtc caa tac ggt tat ggc ggt ttc agc atc tca atc aac      1536
Ala Pro Ala Val Gln Tyr Gly Tyr Gly Gly Phe Ser Ile Ser Ile Asn
            500                 505                 510 ccc ttc ttt agc ccg acc atc ctc act ttc ttg aag aca tac gga gca      1584
Pro Phe Phe Ser Pro Thr Ile Leu Thr Phe Leu Lys Thr Tyr Gly Ala
        515                 520                 525 gtc tac gct gtt gcc aat atc aga ggg gga ggc gag ttt gga gag gag      1632
Val Tyr Ala Val Ala Asn Ile Arg Gly Gly Gly Glu Phe Gly Glu Glu
530                 535                 540 tgg cat gaa aat ggt atg agg gaa aag aag cac aat tgc ttt gac gac      1680
Trp His Glu Asn Gly Met Arg Glu Lys Lys His Asn Cys Phe Asp Asp
545                 550                 555                 560 ttc atc gct gga gcc gag tat ctt gta aag agc aag tat gct gct cca      1728
Phe Ile Ala Gly Ala Glu Tyr Leu Val Lys Ser Lys Tyr Ala Ala Pro
                565                 570                 575 gga aaa gtc acc atc aat ggc ggg tcg aat gga ggt ctc ctt gtt tct      1776
Gly Lys Val Thr Ile Asn Gly Gly Ser Asn Gly Gly Leu Leu Val Ser
            580                 585                 590 gct tgc gtg aat cga gca ccc gaa ggc acg ttc ggt gct gca att gcg      1824
Ala Cys Val Asn Arg Ala Pro Glu Gly Thr Phe Gly Ala Ala Ile Ala
        595                 600                 605 gaa gtt ggt gta cat gat ttg ctt cga ttc cat aaa ttc aca atc gga      1872
Glu Val Gly Val His Asp Leu Leu Arg Phe His Lys Phe Thr Ile Gly
610                 615                 620 cga gcc tgg ata agc gac tac ggt gac ccg gac gat cct aaa gac ttt      1920
Arg Ala Trp Ile Ser Asp Tyr Gly Asp Pro Asp Asp Pro Lys Asp Phe
625                 630                 635                 640 gac ttc atc tat cct atc tcg cca ctg cag aat gtc tcg ccc aca aag      1968
Asp Phe Ile Tyr Pro Ile Ser Pro Leu Gln Asn Val Ser Pro Thr Lys
                645                 650                 655 gtt cta ccg ccc tac atg ctc tca act gct gat cac gac gac cgt gtc      2016
Val Leu Pro Pro Tyr Met Leu Ser Thr Ala Asp His Asp Asp Arg Val
            660                 665                 670 gta ccc agt cac tcg ttc aag atg gca gct act cta caa cat ctg cga      2064
Val Pro Ser His Ser Phe Lys Met Ala Ala Thr Leu Gln His Leu Arg
        675                 680                 685 gcg aac aac cct agt cct att ctc ctg agg gtg gat aag aag gct gga      2112
Ala Asn Asn Pro Ser Pro Ile Leu Leu Arg Val Asp Lys Lys Ala Gly
690                 695                 700 cat ggc gcc ggg aag tcg act aag aag agg gtc gaa gag tcg gcg gat      2160
His Gly Ala Gly Lys Ser Thr Lys Lys Arg Val Glu Glu Ser Ala Asp
705                 710                 715                 720 aag tgg agt ttt gtt gcg cag gct ttg ggc ttg gag tgg aaa gat aaa      2208
Lys Trp Ser Phe Val Ala Gln Ala Leu Gly Leu Glu Trp Lys Asp Lys
                725                 730                 735
```

```
gct aca cta agg gcg agc tca gat ccg gct gct aac aaa gcc cga aag    2256
Ala Thr Leu Arg Ala Ser Ser Asp Pro Ala Ala Asn Lys Ala Arg Lys
        740                 745                 750 gaa gct gag ttg gct gct gcc acc gct gag caa                        2289
Glu Ala Glu Leu Ala Ala Ala Thr Ala Glu Gln
        755                 760
```

<210> SEQ ID NO 10
<211> LENGTH: 763
<212> TYPE: PRT
<213> ORGANISM: Coprinus clastophyllus
<220> FEATURE:
<221> NAME/KEY: misc_feature
<222> LOCATION: (171)..(171)
<223> OTHER INFORMATION: The 'Xaa' at location 171 stands for Tyr.

<400> SEQUENCE: 10

```
Met Val Thr Lys Thr Trp Val Pro Asp Thr Tyr Pro Gln Ala Arg Arg
1               5                   10                  15

Cys Asp His Val Asp Thr Tyr Thr Ser Ala Lys His Gly Glu Val Lys
            20                  25                  30

Val Ala Asp Pro Tyr Arg Trp Met Glu Glu Tyr Thr Asp Glu Thr Asp
        35                  40                  45

Lys Trp Thr Ser Ala Gln Glu Ala Tyr Thr Arg Ala Tyr Ile Asp Lys
    50                  55                  60

Tyr Pro His Arg Gln Arg Leu Glu Asp Ala Phe Met Ala Ser Leu Asp
65                  70                  75                  80

Tyr Ala Arg Ala Gly Ala Pro Val Lys Ser Asp Lys Lys Arg Trp Tyr
                85                  90                  95

Trp Ser Tyr Asn Ser Gly Leu Gln Pro Gln Asn Val Tyr Tyr Arg Ser
            100                 105                 110

Arg Asp Gly Gln Leu Pro Asp Arg Ser Lys Gly Leu Asp Asn Gly Glu
        115                 120                 125

Val Phe Met Asp Met Asn Leu Leu Ser Glu Asp Gly Thr Ala Ala Ile
    130                 135                 140

Ser Val His Ala Phe Ser Asp Asn Gly Glu Tyr Tyr Ala Tyr Gly Val
145                 150                 155                 160

Ser Tyr Ser Gly Ser Asp Phe Thr Thr Val Xaa Ile Arg Arg Thr Asp
                165                 170                 175

Ser Pro Leu Ala Ser Lys Glu Gln Ala Glu Lys Asp Thr Gly Arg Leu
            180                 185                 190

Pro Asp Val Leu Asn Tyr Val Lys Phe Ser Ser Leu Arg Trp Thr Pro
        195                 200                 205

Asp Ser Lys Gly Phe Phe Tyr Gln Arg Tyr Pro Asp His Asn Gly Asn
    210                 215                 220

Thr Gly Ser Asp Lys Pro Ser Asp Ser Gly Ile Glu Thr Arg Gly Asp
225                 230                 235                 240

Lys Asp Ala Met Leu Tyr Tyr His Arg Val Asn Thr Pro Gln Ser Glu
                245                 250                 255

Asp Ile Leu Val Tyr Tyr Asp Lys Thr Lys Pro Asp Trp Met Tyr Gly
            260                 265                 270

Ile Asp Val Thr Asp Asp Lys Tyr Val Val Met Ser Val Val Gln
        275                 280                 285

Asp Thr Ser Arg Lys Asn Leu Leu Trp Ile Ala Glu Leu Thr Asp Asp
    290                 295                 300

Phe Ile Glu Lys Gly Phe Lys Trp Asn Arg Val Met Asp Lys Phe Asp
305                 310                 315                 320
```

-continued

```
Ala Glu Tyr Glu Tyr Ile Lys Asn Glu Gly Pro Val Phe Val Leu Arg
            325                 330                 335

Thr Asn Glu Asn Ala Pro Lys Tyr Lys Val Val Thr Val Asp Val Ser
            340                 345                 350

Lys Asp Asn Glu Val Lys Pro Phe Ile Pro Glu Ser Asp Gly Phe Leu
            355                 360                 365

Glu Ser Ile Tyr Ala Val Asn Lys Gly Asn Asn Phe Val Val Thr Tyr
    370                 375                 380

Lys Arg Asn Val Lys Asp Glu Ile Tyr Val Tyr Ser Lys Glu Gly Lys
385                 390                 395                 400

Glu Leu Glu Arg Leu Val Pro Asp Phe Ile Gly Ser Ala Ser Val Thr
                405                 410                 415

Ala Arg Trp Glu Asp Thr Trp Phe Phe Ile Asn Cys Ser Gly Phe Thr
                420                 425                 430

Thr Pro Gly Thr Ile Gly Arg Tyr Asp Phe Thr Ala Pro Glu Gly Gln
            435                 440                 445

Arg Trp Ser Thr Tyr His Gln Thr Gln Val Asn Gly Leu Asn Pro Glu
            450                 455                 460

Glu Phe Glu Ala Arg Gln Asp Trp Tyr Glu Ser Lys Asp Gly Thr Lys
465                 470                 475                 480

Ile Pro Met Phe Ile Val Arg His Lys Ser Thr Pro Phe Asp Gly Thr
                485                 490                 495

Ala Pro Ala Val Gln Tyr Gly Tyr Gly Gly Phe Ser Ile Ser Ile Asn
            500                 505                 510

Pro Phe Phe Ser Pro Thr Ile Leu Thr Phe Leu Lys Thr Tyr Gly Ala
            515                 520                 525

Val Tyr Ala Val Ala Asn Ile Arg Gly Gly Gly Glu Phe Gly Glu Glu
            530                 535                 540

Trp His Glu Asn Gly Met Arg Glu Lys Lys His Asn Cys Phe Asp Asp
545                 550                 555                 560

Phe Ile Ala Gly Ala Glu Tyr Leu Val Lys Ser Lys Tyr Ala Ala Pro
                565                 570                 575

Gly Lys Val Thr Ile Asn Gly Gly Ser Asn Gly Gly Leu Leu Val Ser
            580                 585                 590

Ala Cys Val Asn Arg Ala Pro Glu Gly Thr Phe Gly Ala Ala Ile Ala
            595                 600                 605

Glu Val Gly Val His Asp Leu Leu Arg Phe His Lys Phe Thr Ile Gly
            610                 615                 620

Arg Ala Trp Ile Ser Asp Tyr Gly Asp Pro Asp Pro Lys Asp Phe
625                 630                 635                 640

Asp Phe Ile Tyr Pro Ile Ser Pro Leu Gln Asn Val Ser Pro Thr Lys
                645                 650                 655

Val Leu Pro Pro Tyr Met Leu Ser Thr Ala Asp His Asp Asp Arg Val
            660                 665                 670

Val Pro Ser His Ser Phe Lys Met Ala Ala Thr Leu Gln His Leu Arg
            675                 680                 685

Ala Asn Asn Pro Ser Pro Ile Leu Leu Arg Val Asp Lys Lys Ala Gly
            690                 695                 700

His Gly Ala Gly Lys Ser Thr Lys Arg Val Glu Glu Ser Ala Asp
705                 710                 715                 720

Lys Trp Ser Phe Val Ala Gln Ala Leu Gly Leu Glu Trp Lys Asp Lys
                725                 730                 735
```

```
Ala Thr Leu Arg Ala Ser Ser Asp Pro Ala Ala Asn Lys Ala Arg Lys
            740                 745                 750

Glu Ala Glu Leu Ala Ala Ala Thr Ala Glu Gln
        755                 760

<210> SEQ ID NO 11
<211> LENGTH: 24
<212> TYPE: PRT
<213> ORGANISM: artificial
<220> FEATURE:
<223> OTHER INFORMATION: synthesized

<400> SEQUENCE: 11

Arg Ala Ser Ser Asp Pro Ala Ala Asn Lys Ala Arg Lys Glu Ala Glu
1               5                   10                  15

Leu Ala Ala Ala Thr Ala Glu Gln
            20
```

US 7,741,094 B2

PROTEIN HAVING PROLYL OLIGOPEPTIDASE ACTIVITY, AND COMPOSITION CONTAINING THE SAME

BACKGROUND OF THE INVENTION

1. Field of the Invention

The present invention relates to a protein isolated from *Coprinus clastophyllus*, especially to a protein isolated from *Coprinus clastophyllus* and having prolyl oligopeptidase activity, the isolated gene sequence thereof, method for producing and use of the same.

2. Description of the Prior Art

Prolyl oligopeptidase (EC 3.4.21.26), also known as prolyl endopeptidase or post-proline cleaving enzyme, cleaves proline containing polypeptides at the carboxyl side of a proline residue (Polgár, Methods Enzymol. 244:188-200; Polgár, Cell. Mol. Life. Sci. 59:349-362).

Prolyl oligopeptidase is widely researched in recently in several application fields. Prolyl oligopeptidase degrades peptides involving memory and learning and thus considered to be connected with amnesia and conditions of degradative memory, including Parkinson's disease. Inhibitors for prolyl oligopeptidase are currently being researched to find therapies thereof (Yoshimoto et al., J. Pharmacobio-Dyn. 10:730-735; Atack et al., Nat. Prod. Res. 19:13-22; Marighetto et al., Learn Mem. 7:159-169; Lee et al., Planta Med. 70:1228-1230; Sorensen et al., Nahrung 48(1):53-56; Atta-ur-Rahman et al., Nat. Prod. Res. 19:13-22; Jarho et al., J. Med. Chem. 48:47772-4782). Researches in other application fields include: using prolyl oligopeptidase as a treatment for celiac disease caused by proline abundant gluten (Piper et al., J. Pharmacol. Exp. Ther. 311:213-219; Marti et al., J. Pharmacol. Exp. Ther. 312:19-26; Matysiak-Budnik et al., Gastroenterol. 129(3):786-796; Pyle et al., Clin. Gastroenterol. Hepatol. 3(7):687-94; Gass et al., Biotechnol. Bioeng. 92(6):674-84); purification and recovery of exogenously expressed peptides (Xiu et al., Biotechnol. Appl. Biochem. 36(Pt2):111-117); and development of a cancer-treating prodrug being less toxic to cells and will be converted by prolyl oligopeptidase to a functional drug (Heinis et al., Biochemistry 43:6293-6303).

Prolyl oligopeptidases found in animals, plants and microbes generally display relatively low activities. Some know prolyl oligopeptidases found in microbes include those originate from: *Flavobacterium meningosepticum* (having an activity of 0.30 U/ml according to Yoshimoto et al., J. Biol. Chem. 255:4786-4792); *lactobacillus casei* (having an activity of 0.15 U/g according to 6. Habibi-Najafi et al., J. Dairy Sci. 77:385-392); *Propionibacterium freudenreichii* (having an activity of 4.3 mU/ml according to Tobiassen et al., J. Dairy Sci. 79:2129-2136); a fermented broth of *Agaricus bisporus* (having an activity of 0.15 U/ml according to Abdus Sattar et al., J. Biochem. 107:256-261); and *Xanthomonas* spp. (having an activity of 0.15 U/ml according to Szwajcer-Dey et al., J. Baceteriol. 174:2454-2459).

Enzymatic activity of prolyl oligopeptidase may be increased by genetic engineering methods, specifically, cloning a prolyl oligopeptidase gene into host cells such as *E. coli* (*Escherichia coli*) followed by exogenous large-scale expression. Prolyl oligopeptidase originally from *Shingomonas capsulata* exhibited 7-fold higher activity of 0.2 U/ml in *E. coli* (Yoshimoto et al., Japanese patent JP10066570). A *Flavobacterium meningosepticum* prolyl oligopeptidase gene encoded protein expressed in *E. coli* exhibits maximal activity of 0.7 U/ml (Diefenthal et al., Appl. Microbiol. Biotechnol. 40:90-97). A *Flavobacterium meningosepticum* prolyl oligopeptidase reconstructed by Uchiyama in *E. coli* exhibits maximal activity of 8.1 U/ml, which further demonstrates specific activity as high as 124 U/mg after purification (Uchiyama et al., J. Biochem. 128:441-447). An *Aeromonas hydrophila* prolyl oligopeptidase expressed in *E. coli* exhibits activity of 1.48 U/ml which is 100 fold higher than expressed in original *Aeromonas hydrophila* strain and exhibits specific activity up to 8.8 U/mg after purification (Kanatani et al., J. Biochem. 113:790-796). An *Aeromonas punctata* prolyl oligopeptidase expressed in *E. coli* has 112 fold higher activity than that expressed in original strain and exhibits specific activity up to 67 U/mg after purification (Li et al., Wei Sheng Wu Xue Bao. 2000 40(3):277-283).

In addition, a *Pyrococcus furious* prolyl oligopeptidase gene encoded protein expressed in *E. coli* exhibits specific activity of 232 U'/mg (the activity units being alternatively defined and calculated as 1 U' being equal to 0.1 $OD_{410}$ per minute by Harwood et al., J. Bacterol. 179:3613-3618 and different from that in aforementioned literatures) and 4 U/mg (Harwood and Schreier et al., Methods Enzymol. 330:445-454) after purification.

Aforementioned examples demonstrate that purified prolyl oligopeptidases expressed in *E. coli* have higher activity. However, prolyl oligopeptidases of different origins have preferences for interaction conditions. Optimum conditions enable a prolyl oligopeptidase to display full activity; otherwise, only partial activity may be attained. A highly active prolyl oligopeptidase has more potential for use if its optimum conditions are similar to practical conditions where it is applied. When evaluating the potential of a prolyl oligopeptidase in such aspect, optimum temperature and optimum pH are considered. Furthermore, ranges of optimum conditions are defined by retained activity under optimum generic environmental conditions. For example, heat stability is determined by measuring the ratio of retained activity after heating to full activity.

Each of the aforementioned prolyl oligopeptidases have corresponding optimum conditions. The optimum conditions for *Aeromonas hydrophila* prolyl oligopeptidase are 30° C. and pH 8.0. When preheated at 42° C. for 30 minutes, 50% activity is retained. The activity of an *Aeromonas* punctata prolyl oligopeptidase reaches optimum activity at 34° C. and pH 8.4. The optimum pH and temperature for *Flavobacterium meningosepticum* prolyl oligopeptidase are 7.0 and 40° C.; and its activity will be reduced to 50% when heated to 42° C. for 15 minutes (Yoshimoto et al., J. Biol. Chem. 255:4786-4792). When heated at 60° C. for 1 hour, the activity of a *Flavobacterium meningosepticum* prolyl oligopeptidase mutated with error-prone PCR mutagenesis drop to 50% under conditions of pH7.0 and 30° C. (Uchiyama et al., J. Biochem. 128:441-447). Of all prolyl oligopeptidases expressed in *E. coli*, *Flavobacterium meningosepticum* prolyl oligopeptidase exhibits the highest specific activity and showed the best heat stability after mutagenesis with error-prone PCR. However, since *Flavobacterium meningosepticum* is a pathogen, safety concerns arise for use, despite other prolyl oligopeptidases exhibiting lower heat-stability.

Nevertheless, to find and isolate a prolyl oligopeptidase corresponding to human usage from various organisms requires much research and experimentation for those generally skilled in the art of the present invention. This difficulty was compounded when the prolyl oligopeptidase found in the first screening of *Aspergillus niger* was later authenticated to be another serine protease. Though certain basidiomycete was known to have prolyl oligopeptidase, there are no filamentous fungi known to have prolyl oligopeptidase so far. As a result, no prolyl oligopeptidase of fungal original has been expressed in *E. coli* in large scale.

To overcome the shortcomings of available prolyl oligopeptidases, the present invention provides a protein having prolyl oligopeptidase activity, a nucleic acid encoding thereof and methods for producing and using the same to mitigate or obviate the aforementioned problems.

SUMMARY OF THE INVENTION

The present invention relates to proteins isolated from *Coprinus clastophyllus* having prolyl oligopeptidase activity, nucleic acids encoding the protein and methods for producing and using the protein.

One aspect of the present invention is to provide an isolated protein selected from the group consisting of:

(a) a protein comprising the amino acid sequence of SEQ ID NO:6 or SEQ ID NO:10;

(b) a protein encoded by a nucleic acid of the sequence of SEQ ID NO:5 or SEQ ID NO:9;

(c) a protein comprising the function of protein (a) or protein (b), and comprising an amino acid sequence having a similarity greater than 60% to the amino acid sequence of protein (a) or protein (b);

(d) a protein comprising the function of protein (c), and encoded by a nucleic acid of a sequence having a similarity greater than 60% to the sequence of SEQ ID NO:5 or SEQ ID NO:9;

(e) a protein encoded by a nucleic acid being able to hybrid to a nucleic acid of the sequence of SEQ ID NO:5 or SEQ ID NO:9 under a highly-strict condition comprising acts of allowing interaction at 50° C. for 16 hours; washing with a solution having 2×SSC and 0.1% SDS at room temperature for 5 minutes; repeating the preceding act once; allowing interaction in a solution having 0.5×SSC and 0.1% SDS at 65° C. for 15 minutes; and repeating the preceding act once.

Another aspect of the present invention is to provide isolated nucleic acids selected from the group consisting of:

(a) a nucleic acid encoding the aforementioned protein;

(b) a nucleic acid of the sequence of SEQ ID NO:5 or SEQ ID NO:9;

(c) a nucleic acid encoding a protein as that encoded by nucleic acid (b), and of a sequence having a similarity greater than 60% to nucleic acid (b);

(d) a nucleic acid being able to hybrid to a nucleic acid of the sequence of each of nucleic acid (a)-(c) under a highly-strict condition comprising acts of allowing interaction at 50° C. for 16 hours; washing with a solution having 2×SSC and 0.1% SDS at room temperature for 5 minutes; repeating the preceding act once; allowing interaction in a solution having 0.5×SSC and 0.1% SDS at 65° C. for 15 minutes; and repeating the preceding act once;

(e) a nucleic acid encoding a protein comprising a amino acid sequence identical to the amino acid sequence of the protein encoded by each of nucleic acids (a)-(d); and (f) a nucleic acid of the complementary sequence of each of nucleic acid (a)-(e).

The present invention also relates to nucleic acid probes, chimeric genes, nucleic acid constructs, vectors, transformants, pharmaceutical compositions, composition for use with a proline containing prodrug, as well as use of the aforementioned protein.

Another aspect of the present invention provides methods for producing a protein having prolyl oligopeptidase activity comprising (a) providing the aforementioned transformant; (b) culturing the transformant in a condition allowing expression of a protein having prolyl oligopeptidase activity; and (c) purifying and acquiring the protein.

Other objectives, advantages and novel features of the invention will become more apparent from the following detailed description when taken in conjunction with the accompanying drawings.

DETAILED DESCRIPTION OF THE PREFERRED EMBODIMENTS

Definitions

Figure 1:
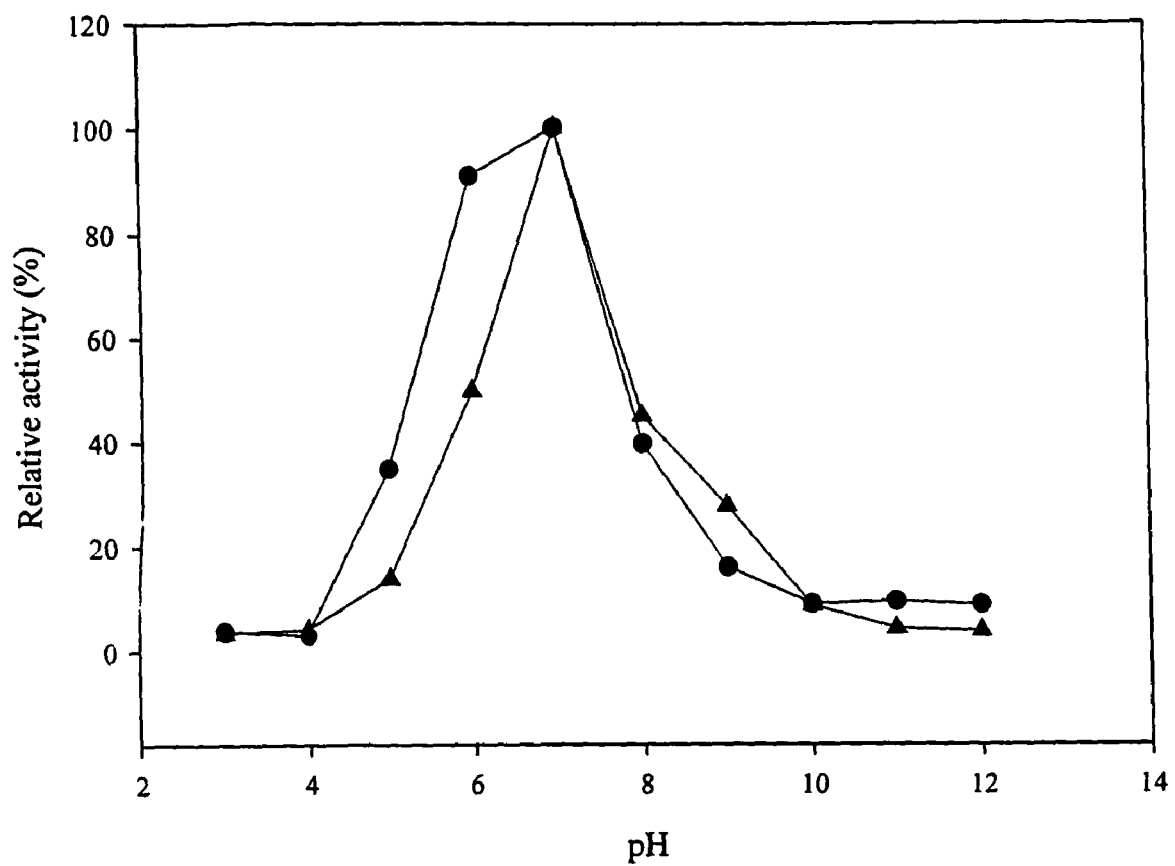
FIG. 1 is a line graph of prolyl oligopeptidase activities of proteins pProHN14 and pProHN17 versus pH values wherein solid circles represent the pProHN14 protein and solid triangles represent the pProHN17 protein.

Identity: The term "identity" is defined herein as the invariant extent between two nucleic acid sequences or that between two amino acid sequences. In the context of the present invention, "identity" refers to the "Identity" score when comparing two sequences (nucleic acid or amino acid) with Gap program (Genetics Computer Group, Version 11.1), wherein gap creation penalty=8 and gap extension penaly=2.

Similarity: The term "similarity" is defined herein as the extent of relatedness between two nucleic acid sequences or that between two amino acid sequences. The similarity between two sequences can be obtained from, the ratio of identity or conservation between the two sequences, or both. In the context of the present invention, "similarity" refers to the "Similarity" score when comparing two sequences (nucleic acid or amino acid) with Gap program (Genetics Computer Group, Version 11.1), wherein gap creation penalty=8 and gap extension penaly=2.

Chimeric gene: The term "chimeric gene" is defined herein as a gene formed by a recombinant nucleic acid carrying nucleic acids of different origins. For example, a chimeric gene may be formed by a recombinant nucleic acid carrying nucleic acids of different genes, or recombined nucleic acids of different gene fragments.

Control sequence: The term "control sequence" is defined herein as a nucleic acid sequence defining the on or off states of a gene and controlling the expression of the nucleic acid thereof.

Vector: The term "vector" is defined herein as a vehicle transferring a nucleic acid molecule into a host cell, which may be a plasmid, a phage or a virus. Such vectors include but are not limited to expression vectors that routinely accept nucleic acid molecules with recombinant nucleic acid sequences and induce the expression of the nucleic acid sequence after transferring the nucleic acid molecules into a host cell. Corresponding vectors for a host cell are determined by the vector-cell compatibility. Furthermore, the aforementioned plasmid may be a linear or a closed circular nucleic acid molecule.

DETAILED DESCRIPTION OF THE INVENTION

Prolyl oligopeptidase is researched for having valuable potentials such as to degrade peptides involving memory and learning, to be used as a treatment for celiac disease caused by proline abundant gluten, to purify or recover exogenously expressed peptides and may be used as a helping agent for cancer-treating prodrugs.

In the present invention, proteins with prolyl oligopeptidase activity and gene sequences thereof are described. Data relevant to the producing of said protein and substantial practical acts are also provided. The protein provides high enzymatic activity and a range of optimum conditions suitable for various applications.

In another aspect of the present invention, the isolated prolyl oligopeptidase gene from *Coprinus clastophyllus* is demonstrated being used in pharmaceutical applications with methods disclosed herein.

The aforementioned protein with prolyl oligopeptidase activity can be used as a treatment for celiac disease caused by proline abundant gluten, as a helping agent for cancer-treating prodrugs or for purifying and recovering exogenously expressed peptides.

The nucleic acids, vectors and transformants relevant to the aforementioned protein and methods are also disclosed.

It will be understood by those skilled in the art that various modifications, such as minor variations of concentrations or activities of produced prolyl oligopeptidases may be made to the present invention without departing from the spirit and scope of the invention. Furthermore, the present invention is not limited to the examples described herein but may also encompasses any and all embodiments within the scope of the present invention. It is also to be understood by those skilled in the art that alternatively available biological methods and techniques may be applied without departing from the scope of the invention.

Proteins

The present invention relates to isolated proteins having prolyl oligopeptidase activity. Prolyl oligopeptidase cDNAs are cloned from previously isolated *Coprinus clastophyllus* strain (deposition number: BCRC 36074; Bioresource Collection and Research Centre, Food Industry Research and Development Institute, Taiwan) having heat-stable prolyl oligopeptidase (extrocellular activity 0.03 U/ml). To further raise the prolyl oligopeptidase activity, *E. coli* was used as a host cell to hold the cloned prolyl oligopeptidase cDNA for large-scale expression in order to obtain functional amounts of the protein.

As defined herein, 1 U of prolyl oligopeptidase activity is the capability to produce 1 μmole of p-nitroaniline per minute. In a preferred aspect, the intracellular prolyl oligopeptidase activity of the protein is 7.2 U/ml, in another preferred aspect, 7.7 U/ml. The protein may be purified. The specific activity of the purified protein may be 55.0 U/mg to 70.0 U/mg. In a more preferred aspect, the specific activity of the purified protein may be 56.1 U/mg to 70.0 U/mg. In another preferred aspect, the specific activity of the purified protein may be 56.1 U/mg or 66.8 U/mg.

The optimum pH value for the protein may be pH 6 to pH 8. In a preferred aspect, the optimum pH value for the protein may be pH 6 to pH 7 and in a most preferred aspect, the optimum pH value for the protein may be pH 7. The optimum temperature for the protein at pH 7 may be 45° C. The optimum temperature for the protein at pH 8 may be 37° C.

In a preferred aspect, the protein contains an amino acid sequence having a similarity greater than 60% to the sequence of SEQ ID NO:6 or SEQ ID NO:10 or is encoded by a nucleic acid of a sequence having a similarity greater than 60% to the sequence of SEQ ID NO:5 or SEQ ID NO:9. In another preferred aspect, the similarities of the amino acid sequence or the nucleic acid sequence are greater than 70%. In a more preferred aspect, the similarities of the amino acid sequence or the nucleic acid sequence are greater than 80%. In an even more preferred aspect, the similarities of the amino acid sequence or the nucleic acid sequence are greater than 90%. In a most preferred aspect, the similarities of the amino acid sequence or the nucleic acid sequence are greater than 95%. It is understood by those skilled in the art that there may be variations between the aforementioned proteins in accordance with the present invention without abolishing the prolyl oligopeptidase activities thereof. Thus, it is also understood by a person skilled in the art that varying proteins having the aforementioned prolyl oligopeptidase activity are also covered within the scope of the present invention. In another most preferred aspect, the protein has an amino acid sequence comprising SEQ ID NO:6 or SEQ ID NO:10 or is encoded by a nucleic acid containing the sequence of SEQ ID NO:5 or SEQ ID NO:9.

In another preferred aspect, the protein has the function of the aforementioned protein and is encoded by a nucleic acid of a sequence having a similarity greater than 60% to the sequence of SEQ ID NO:5 or SEQ ID NO:9.

In another preferred aspect, the protein has the function of the aforementioned protein and is encoded by a nucleic acid wherein the nucleic acid hybrids to another nucleic acid of the sequence of SEQ ID NO:5 or SEQ ID NO:9 under highly-strict conditions comprising acts of allowing interaction at 50° C. for 16 hours; washing with a solution having 2×SSC and 0.1% SDS at room temperature for 5 minutes; washing with a solution having 2×SSC and 0.1% SDS at room temperature for 5 minutes; allowing interaction in a solution having 0.5×SSC and 0.1% SDS at 65° C. for 15 minutes; allowing interaction in a solution having 0.5×SSC and 0.1% SDS at 65° C. for 15 minutes.

Nucleic Acids

The present invention also relates to isolated nucleic acids of sequences encoding the aforementioned proteins. In a preferred aspect, the nucleic acid is a nucleic acid of a sequence having a similarity greater than 60% to the sequences of SEQ ID NO:5 or SEQ ID NO:9 and encodes a protein having the prolyl oligopeptidase activity as that of the aforementioned protein. In another preferred aspect of the present invention, the similarity of the sequence of the nucleic acid with the sequences of SEQ ID NO:5 or SEQ ID NO:9 is greater than 70%; in an more preferred aspect the similarity is greater than 80%; in a even more preferred aspect the similarity is greater than 90%; in a most preferred aspect the similarity is greater than 95%. In another most preferred aspect, the sequence of the nucleic acid comprises SEQ ID NO:5 or SEQ ID NO:9.

It is to be understood by those skilled in the art that there may be variations between the sequence of SEQ ID NO:5 or SEQ ID NO:9 and the sequences of aforementioned nucleic acids. Each of the nucleic acid variants encodes a protein having prolyl oligopeptidase activity expressed by the sequences of SEQ ID NO:6 or SEQ ID NO:10, or of a sequence having a considerable similarity to the sequences of SEQ ID NO:6 or SEQ ID NO:10. Thus a person with general skill in the art can easily understand that those nucleic acids are within the scope of the present invention as long as the function of the encoded protein will not be abolished by the sequence variations.

Those skilled in the art will also understand that nucleic acids encoding a protein of the same amino acid sequence of that of the proteins encoded by the aforementioned nucleic acids is within the scope of the present invention. Furthermore, nucleic acids of complementary (antisense) sequences do not depart from the spirit and scope of the present invention.

Nucleic Acid Probes

The present invention also relates to nucleic acid probes that hybrid to the aforementioned nucleic acids under highly strict conditions comprising acts of: allowing interaction at 50° C. for 16 hours; washing with a solution having 2×SSC and 0.1% SDS at room temperature for 5 minutes; washing with a solution having 2×SSC and 0.1% SDS at room temperature for 5 minutes; allowing interaction in a solution having 0.5×SSC and 0.1% SDS at 65° C. for 15 minutes; allowing interaction in a solution having 0.5×SSC and 0.1% SDS at 65° C. for 15 minutes.

Chimeric Genes

The present invention also relates to chimeric genes comprising the aforementioned nucleic acids being operably linked to a promoter allowing expression in a host cell. In an application of a research or commercial purpose, the skill necessary to operably link a nucleic acid and a promoter to achieve the purpose is well understood by those skilled in the art of the present invention.

Nucleic Acid Constructs and Vectors

The present invention also relates to nucleic acid constructs comprising the aforementioned nucleic acids being operably linked to a control sequence allowing the expression of the protein encoded by the nucleic acid in a host cell. Such nucleic acid constructs, such as recombinant plasmids, are widely applied in research or commercial fields. Building a nucleic acid construct containing a specific nucleic acid is understood and practicable to a person with general skill in the art.

The present invention also relates to vectors comprising the aforementioned nucleic acids or the aforementioned nucleic acid constructs.

Transformants

The present invention also relates to transformants being a host cell holding nucleic acids in accordance with the present invention wherein the host cell is transformed by accepting the aforementioned nucleic acids. The host cell may be an *E. coli* cell. For example, the host cell may be an *E. coli* cell of BL21(DE3) strain or DH10B strain. In another preferred aspect of the present invention, the prolyl oligopeptidase cDNA is operably linked to a promoter or a control sequence allowing expression in a host cell to form a chimeric gene or a nucleic acid construct. The chimeric gene or nucleic acid construct is able to express the cDNA in a host cell.

Compositions

The present invention also relates to compositions, such as pharmaceutical compositions. The compositions comprise the aforementioned protein in accordance with the present invention as a functional component. Prolyl oligopeptidase is known to be used as a treatment for celiac disease caused by proline abundant gluten. In addition, the range of the optimum conditions of the protein having prolyl oligopeptidase in accordance with the present invention covers conditions not covered by optimum conditions of known prolyl oligopeptidases, and is suitable for use under such conditions. As a functional component of the aforementioned composition, the protein effectively allows the purpose of the composition to be achieved. In an aspect of the present invention, the composition also comprises an excipient allowing the composition to be made as a solid matter, a semi-solid matter or a liquid matter.

The composition in accordance with the present invention may also be used with a prodrug containing proline residues. The composition for use with the proline-containing prodrug has at least one pharmaceutically acceptable excipient and the aforementioned protein. Having prolyl oligopeptidase activity, the protein is used as a functional component for converting the prodrug to a functional drug. In a preferred aspect, the composition further comprises an antibody conjugated with the aforementioned protein. The antibody is used to anchor the protein in a target tissue of an organism. When the prodrug is later administered into the circulatory system of the organism, the protein will only interact with the prodrug delivered to the target tissue. With the prolyl oligopeptidase activity of the protein, the prodrug will be converted into a functional drug in the target tissue, which significantly raises the selectivity and accuracy of the prodrug.

Use of the Aforementioned Protein

One aspect of the present invention relates to using the aforementioned protein. With the prolyl oligopeptidase activity, the protein can be used to process exogenously expressed peptides for recovering or be used in the manufacture of a purification reagent thereof.

Methods for Producing a Protein Having Prolyl Oligopeptidase Activity

The present invention also relates to methods for producing proteins having prolyl oligopeptidase activity. The method comprises providing the aforementioned transformant; culturing the transformant in a condition allowing expression of a protein having prolyl oligopeptidase activity; and purifying and obtaining the protein. The host cell includes, but is not limited to, a transformed cell of BL21(DE3) *E. coli* strain or DH10B *E. coli* strain.

EXAMPLES

The following experimental designs are illustrative, and are not intended to limit the scope of the present invention. Reasonable variations, such as those occurring to a person reasonably skilled in the art can be made herein without departing from the scope of the present invention.

Example 1

Construction of *Coprinus clastophyllus* cDNA Library and Cloning of Prolyl Oligopeptidase cDNA 1. Cloning of *Coprinus clastophyllus* Prolyl Oligopeptidase gene Fragments and Preparation of Probes Fungal genomic sequences were searched on NCBI web site by BLAST with the amino acid sequence of human prolyl oligopeptidase. Polymerase chain reaction (PCR) primers Pro16 and Pro17 were designed from regions of the genomes of *Coprinopsis cinerea* okayama7#130 and *Phanerochaete chrysosporium* RP-78 where high similarity to the prolyl oligopeptidase sequence was observed and have been attached, respectively as:

```
Pro16: 5'-tacggcggmt tcascatctc-3'    (SEQ ID NO: 1)

Pro17: 5'-tgccaytcyt cwccraactc-3'    (SEQ ID NO: 2)
```

The genomes of *Coprinopsis cinerea* okayama7#130 and *Phanerochaete chrysosporium* RP-78 are freely publicly available in databases maintained by U.S. National Center for Biotechnology Information (Bethesda, Md.

PCR was carried out using PCR primers Pro16 and Pro17 and genomic DNA of *Coprinus clastophyllus* as a template. 50 µl of mix solution for PCR comprises 1×PCR buffer, 0.2 mM of dNTP, 1 µM of Pro16, 1 µM of Pro17, 5 U of pfu DNA polymerase (Roach) and the template (genomic DNA of *Coprinus clastophyllus*). PCR was carried out with ABI 9700 thermocycler (Applied Bioscience) and the following PCR program.

PCR program:
94° C., 3 minutes [1 repeat];
94° C., 30 seconds, 64° C., 30 seconds, 72° C., 1 minute [5 repeats];
94° C., 30 seconds, 60° C., 30 seconds, 72° C., 1 minute [5 repeats];
94° C., 30 seconds, 56° C., 30 seconds, 72° C., 1 minute [35 repeats];
72° C., 7 minutes [1 repeat].

A 128 bp (base pair) fragment was amplified using PCR. The amplified fragment was then cloned into a PCR®2.1-TOPO vector (Invitrogen) to obtain a plasmid referred to as 'p128'.

Two primers Pro20 and Pro21 were designed from p128. A probe was made from the Pro20 and Pro21 primers with PCR DIG Labeling Kit (Roche) following the manual of the kit. A PCR program was used in making the probe.

```
Pro20:  5'-tacggcggat tcagcatctc-3'   (SEQ ID NO: 3)

Pro21:  5'-tgccactcct caccaaactc-3'   (SEQ ID NO: 4)
```

PCR program:
94° C., 3 minutes [1 repeat];
94° C., 30 seconds, 58° C., 30 seconds, 72° C., 40 seconds [35 repeats];
72° C., 7 minutes [1 repeat].

2. Cultivation of Strains

*Coprinus clastophyllus* was cultured in YMA plate (Difco, No. 0712) at 25° C. for 18 days and then transferred to medium N at 25° C. and shaken at 200 rpm for 7 days. Medium N was adjusted to pH6 and comprised 2% glucose (Merck), 0.3% soybean flour, 1% Tryptone, 0.3% $KH_2PO_4$ (Merck) and 0.1% $MgSO_4$ (Merck).

3. Building *Coprinus clastophyllus* cDNA Library 1.2 g of dehydrated mycelium was taken on day 7 of the aforementioned *Coprinus clastophyllus* cultivation and total RNA was extracted with TRIZOL (Invitrogen) according to the operation process provided therewith.

325 µg of *Coprinus clastophyllus* total RNA was obtained wherein the ratio of $OD_{260}/OD_{280}$ was 2.05. The amount of total RNA to be extracted may be up to 500 µg.

An mRNA isolation kit, such as PolyATtract® mRNA Isolation Systems Kit provided by Promega, was used to extract mRNA from the total RNA according to the operation process provided with the kit. 6 µg of mRNA (with polyA) was obtained, wherein the ratio of $OD_{260}/OD_{280}$ was 2.01. The aforementioned PolyATtract® mRNA Isolation Systems Kit primarily comprises 50 µl Biotinylated Oligo(dT) Probe (50 pmol/µl), 2.8 ml 20×SSC Solution (2×1.4 ml), 9 ml Streptavidin MagneSphere® Paramagnetic Particles (15×0.6 ml), 50 ml Nuclease-Free Water (2×25 ml), 1 each MagneSphere® Magnetic Separation Stand for 1.5 ml. The aforementioned mRNA extraction was carried out with magnetic separation technology (MagneSphere® technology). Other mRNA isolation kits able to extract mRNA from total RNA may also be employed.

ZAP-cDNA® Gigapack®III Gold Cloning Kit (Stratagen) was used according to operation process provided therewith. DNA fragments having lengths within 0.75-3 kb were collected as cDNAs with the ZAP-cDNA® Gigapack®III Gold Cloning Kit. $8 \times 10^5$ plasmid-carrying plaques were screened as a collection of strains defining a *Coprinus clastophyllus* cDNA library.

Different plasmids were respectively carried by the strains in the *Coprinus clastophyllus* cDNA library. Each plasmid comprised at least one vector and at least one cDNA. Each of the at least one vector comprised multiple restriction sites. The multiple restriction sites at least include EcoRI and HindIII sites. In addition, the sequences of regions flanking the two ends of the cDNA respectively correspond to T3 primer and T7 primer.

4. Plaque Selection

Plaque hybridization was carried out according to the following operation process of ZAP-cDNA® Gigapack®III Gold Cloning Kit to obtain multiple plaques formed with helper phage. A plaque lift was made with nitrocellulose membrane.

The plaque lift was first prehybridized in a Southern-blot hybridization solution such as the FastHyb solution (Biochain) at 50° C. for 2 hours and then undergones hybridization in a probe-containing FastHyb solution at 50° C. for 16 hours.

The plaque lift was then washed as follows:

(1) washing with a solution having 2×SSC and 0.1% SDS at room temperature for 5 minutes;

(2) repeating act (1) washing with a solution having 2×SSC and 0.1% SDS at room temperature for 5 minutes once;

(3) allowing interaction in a solution having 0.5×SSC and 0.1% SDS at 65° C. for 15 minutes; and (4) repeating act (3) allowing interaction in a solution having 0.5×SSC and 0.1% SDS at 65° C. for 15 minutes once.

The DIG antibodies conjugated with the probes were then detected after washing the plaque lift. The detection was visualized on X-ray films with autoradio development signals to identify plaques.

5. Obtaining Transformant

With the aforementioned process, 93 significant signals were identified. A secondary selection was carried out using ZAP-cDNA® Gigapack®III Gold Cloning Kit according to its operation process to further screen a pure single plaque. T3 primer and T7 primer were used to obtain PCR products from the plaques. PCR products having first 11 largest molecular weight were amplified from 11 plaques. The 11 plaques were selected and processed with in vivo excision.

The plasmid obtained from the 11 plaques were confirmed with EcoRI and HindIII restriction enzymes and then analyzed with gel electrophoresis. 4 longest plasmids, 49-1, 71-1, 76-3 and 91-1, were picked for producing transformants.

6. Sequencing

The lateral region of cDNA carried by aforementioned plasmids were first sequenced using available primers such as T3 and T7. Primers were further designed from sequences of lateral regions to sequence nested regions to complete the full length of the cDNA.

7. Obtaining and Confirming *Coprinus clastophyllus* Prolyl Oligopeptidase cDNA

The nucleic acid sequence of *Coprinus* clastophyllus prolyl oligopeptidase cDNA (SEQ ID NO:5) shows that the full length is 2508 nt (nucleotides) and a 2217 nt long ORF (open reading frame) (SEQ ID NO:6) starts at 65th nt of the cDNA. The ORF encodes a 83.9 kD protein having 739 amino acids and prolyl oligopeptidase activity.

With reference to Table 1, the amino acid sequence of *Coprinus clastophyllus* prolyl oligopeptidase was aligned with amino acid sequences of prolyl oligopeptidases from other species using the GAP utility of GCG software (Accelrys). A highest identity (45.8%) to *Xenopus tropicalis* and a secondary highest identity (44.7%) to *ustilago maydis* were observed. Though *Coprinus clastophyllus* and *Cryptococcus neoformans* belong to the same genus, identities in a range between 40%-43.9% for human, mouse, pig, blue-green algae, *Arabidopsis thaliana* or bovine were higher than the identities in a range between 31.6%-32% to *Cryptococcus neoformans*.

Table 1. Similarities and identities of prolyl oligopeptidase amino acid sequences between *Coprinus clastophyllus* and other species

TABLE 1

Similarities and identities of prolyl oligopeptidase amino acid sequences between *Coprinus clastophyllus* and other species

| Species | Similarity (%) | Identity (%) |
|---|---|---|
| Xenopus tropicalis | 54.6 | 45.8 |
| Ustilago maydis | 54.2 | 44.6 |
| Anabaena variabilis | 55.1 | 43.9 |
| Human | 54.6 | 43.8 |
| Human-2 | 54.5 | 43.7 |
| Mouse | 53.7 | 43.5 |
| Rat | 53.5 | 43.5 |
| Pig | 54.0 | 43.2 |
| Nostoc sp. | 54.9 | 43.2 |
| Oryza sativa | 53.2 | 43.2 |
| Arabidopsis thaliana | 52.6 | 43.2 |
| Bovine | 53.2 | 43.0 |
| Deinococcus radiodurans | 49.6 | 39.9 |
| Aeromonas punctata | 50.8 | 39.2 |
| Aeromonas hydrophila | 49.9 | 38.6 |
| Novosphingobium capsulatum | 47.2 | 37.7 |
| Flavobacterium meningosepticum | 47.4 | 37.6 |
| Pyrococcus horikoshii | 45.2 | 34.9 |
| Pyrococcus abyssi | 46.6 | 34.6 |
| Pyrococcus furiosus | 44.9 | 33.2 |
| Cryptococcus neoformans | 44.5 | 32.0 |
| Cryptococcus neoformans-2 | 42.2 | 31.6 |
| Pseudomonas entomophila | 36.0 | 28.5 |
| Neisseria menigitidis | 34.9 | 27.1 |

It is observed that various proteins of amino acid sequences having similarity lower than 60% to the amino acid sequence of SEQ ID NO:6 encoded by nucleic acid SEQ ID NO:5. Variations of amino acid sequences do not necessarily alter the prolyl oligopeptidase activities. Thus it will be understood by a person skilled in the art that proteins having the aforementioned prololigopeptidase activities as in the present invention may also have similarities greater than 60% therewith. These varying proteins are also covered within the scope of the present invention.

Example 2

Expression of *Coprinus clastophyllus* Prolyl Oligopeptidase cDNA in *E. coli*

Primers Pro31 and Pro32 were designed to generate a stop codon in an amplified full-length prolyl oligopeptidase cDNA using PCR with pfu DNA polymerase.

```
Pro 31:
5'-atggtgacca aaacctgggt-3'        (SEQ ID NO: 7)

Pro 32:
5'-ctagagtgta gctttatctt tc-3'     (SEQ ID NO: 8)
```

PCR program:
94° C., 3 minutes [1 repeat];
94° C., 30 seconds, 58° C., 30 seconds, 72° C., 180 seconds [35 repeats];
72° C., 3 minutes [1 repeat].

The amplified full-length prolyl oligopeptidase cDNA was ligated into an expression vector pET 151/D-TOPO (Invitrogen) comprising a T7 primer corresponding sequence and an N-terminal His-tag. A recombinant construct was obtained as a result of the ligation. The recombinant construct was then used to transform host cells. The host cells were DH10B *E. coli* strain cells (Invitrogen). The host cells were cultured at 37° C. in LB broth (USB) or on LB plates (USB). Multiple colonies were obtained and 3 colonies were further selected. Recombinant plasmids were obtained from the cells of the selected colonies. The recombinant plasmids were further used to transform host cells, being BL21(DE3) *E. coli* strain cells (Invitrogen), for expression.

The BL21(DE3) host cells were divided into 3 groups each group was respectively transformed with the recombinant plasmids obtained from the 3 colonies which were further selected. The BL21(DE3) host cells were added to shaking flasks containing LB broth and the densities of $OD_{600}$ readings were within 0.4-0.6.0.4 mM (final concentration) of IPTG was added into each flask and the cultivation lasted for another 20 hours thereafter. *Coprinus clostophyllus* prolyl oligopeptidase cDNAs carried by the recombinant plasmids were expressed in the BL21(DE3) host cells. The expressed proteins having prolyl oligopeptidase activities were purified according the purification methods disclosed in the manual of the pET system (Novagen). Bio-Rad Protein Assay (Bio Rad) was used to measure masses of the expressed proteins. Standard curves were plotted using BSA (bovine serum albumin) as standard to determine masses of the expressed proteins.

Example 3

Measuring Activity of *Coprinus clastophyllus* Prolyl Oligopeptidase

1. Selecting pProHN14 and pProHN17 and Measuring Prolyl Oligopeptidase Activities of Proteins Encoded Thereby 400 µl of 0.1 M Na-phosphate buffer, 50 µl of 10 mM Z-glycyl-L-proline-4-nitroanilide (Fluka) and 50 µl of diluted solution of the aforementioned protein having prolyl oligopeptidase activity were added into a micro centrifuge tube. The mixture was allowed to react for 5 to 60 minutes. 500 µl of 1N HCL quenching solution was added to quench the reaction. After 13000 rpm centrifugation for 5 minutes, the supernatant was obtained to measure the reading of $OD_{410}$.

The amount of p-nitroaniline was determined with a stand curve of $OD_{410}$ readings versus p-nitroaniline amounts. At pH 7.0 and 45° C., 1 U of prolyl oligopeptidase activity was defined as the ability to generate 111 mole of p-nitroaniline per minute.

The reading of $OD_{410}$ was than used to determine the prolyl oligopeptidase activities shown in the aforementioned 3 groups of BL21(DE3) host cells. The 2 groups having highest prolyl oligopeptidase activities were selected. The recombinant plasmids carried in the 2 groups of BL21(DE3) host cells were pProHN14 and pProHN17. The proteins respectively encoded by pProHN14 and pProHN17 showed prolyl oligopeptidase activities of 7.2 U/ml and 7.7 U/ml.

2. Sequencing pProHN14 and pProHN17

The recombinant plasmids, pProHN14 and pProHN17, were sequenced with available sequencing techniques to those skilled in the art. The sequence of pProHN17 was shown in the nucleic acid sequence of SEQ ID NO:5 as predicted.

In addition, the nucleic acid sequence of pProHN14 is shown in SEQ ID NO: 9. It was observed by comparing SEQ ID NO:5 and SEQ ID NO:9 that 4 nucleotides (CTAG) were deleted in the C-terminal of pProHN14 and frame-shift were induced. Consequently, 24 amino acids (R ASSDPAANKA RKEAELAAAT AEQ (SEQ ID NO: 11) were added to the C-terminal of the protein expressed from pProHN 14. The amino acid sequence of the protein expressed from pProHN14 was is shown in SEQ ID NO:10.

In an aspect of the present invention, a DNA fragment having the sequence of pProHN14 (SEQ ID NO:9), is obtained from BCRC 36074 as a PCR template, using a PCR primer having the aforementioned 4 nucleotides (CTAG) deleted. The DNA fragment has the nucleic acid sequence of SEQ ID NO:9. By expressing the DNA fragment with an expression vector, a protein having amino acid sequence of SEQ ID NO:10 is obtained. In a preferred aspect of the present invention, pET151/D-TOPO is used as the expression vector.

3. Comparison of Activities and Specific Activities of Known Prolyl Oligopeptidase and that of Proteins Encoded by pProHN14 and pProHN17

The proteins expressed from pProHN14 and pProHN17 in host cells of BL21(DE3) *E. coli* strain exhibit prolyl oligopeptidase activities of 7.2 U/ml and 7.7 U/ml, which is similar to the activity (8.1 U/ml) of *Flavobacterium meningosepticum* prolyl oligopeptidase and is superior to most known prolyl oligopeptidase.

Ni-NTA affinity column packed with Ni-NTA gel was commercially available in Invitrogen. The Ni-NTA affinity column was used to purify proteins expressed from pProHN14 and pProHN17. Purified proteins of pProHN14 and pProHN17 were observed to have specific activities of 56.1 U/mg and 66.8 U/mg, which were lower than the specific activity of *Flavobacterium meningosepticum* prolyl oligopeptidase but higher than most known prolyl oligopeptidase.

Example 4

Analysis Basic Properties of Proteins Encoded by pProHN14 and pProHN17

1. Optimum pH for *Coprinus clastophyllus* Prolyl Oligopeptidases

The aforementioned method for determining prolyl oligopeptidase activity was used to determine an optimum pH value using pH 3-8 citric acid-$Na_2HPO_4$ buffer solution or pH 9-12 glycine-NaOH buffer solution.

The proteins expressed from pProHN14 and pProHN17 demonstrated highest prolyl oligopeptidase activity at pH 7.0. With reference to FIG. 1, the protein of pProHN14 demonstrated a wider range of optimum pH. The protein of pProHN14 exhibited 90% activity while the protein of pProHN17 exhibited only 50% at pH 6.0.

2. Optimum Temperature for *Coprinus clastophyllus* Prolyl Oligopeptidases

Optimum temperature was determined by measuring prolyl oligopeptidase activities at 25° C., 30° C., 37° C., 45° C. or 45° C. with the aforementioned method for determining prolyl oligopeptidase activity.

Figure 2:
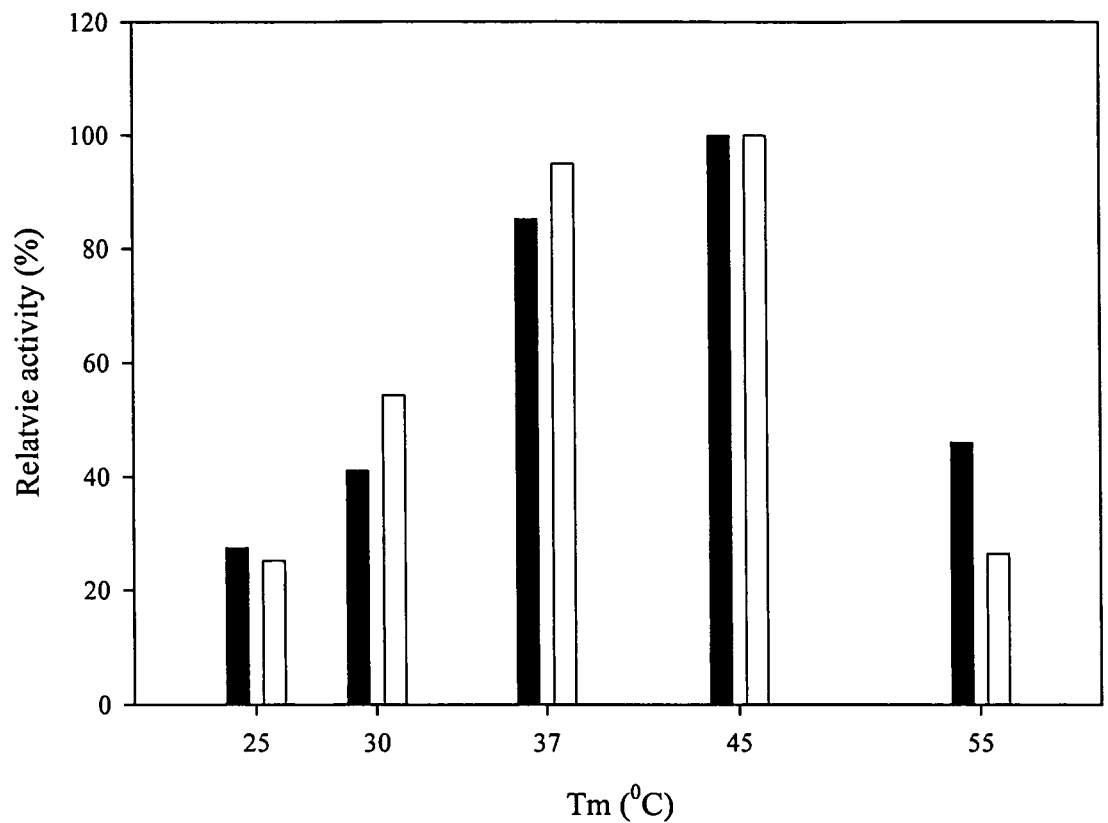
FIG. 2 is a bar chart of the prolyl oligopeptidase activities of proteins pProHN14 and pProHN17 versus temperature at pH 7.0 wherein black bars represent the pProHN14 protein and white bars represent the pProHN17 protein.

With reference to FIG. 2, at pH 7.0, the proteins of pProHN14 and pProHN17 exhibited highest activity at 45° C. Thus the optimum temperature was determined to be 45° C., which is higher than the optimum temperatures of prolyl oligopeptidases known to show high activities.

Figure 3:
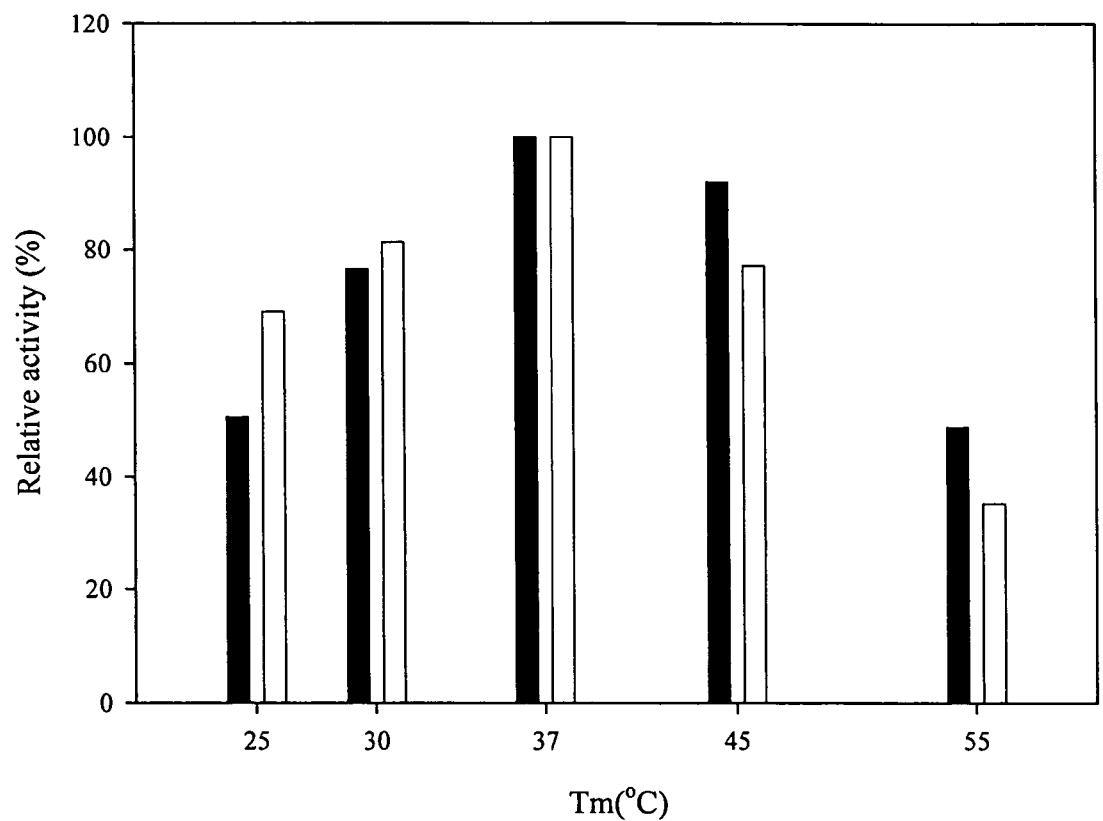
FIG. 3 is a bar chart of the prolyl oligopeptidase activities of proteins pProHN14 and pProHN17 versus temperature at pH 8.0 wherein black bars represent the pProHN14 protein and white bars represent the pProHN17 protein.

With reference to FIG. 3, at pH 8.0, the proteins of pProHN14 and pProHN17 exhibited highest activity at 37° C.

3. Heat Stability *Coprinus clastophyllus* Prolyl Oligopeptidases

The proteins of pProHN14 and pProHN17 were preheated at 30° C., 37° C. or 45° C. for 0, 20, 40, 60 or 80 minutes or preheated at 55° C. for 0, 5, 10 15, 20, 25 or 30 minutes. The activities of preheated proteins were then measured with the aforementioned method for determining prolyl oligopeptidase activity.

Figure 4:
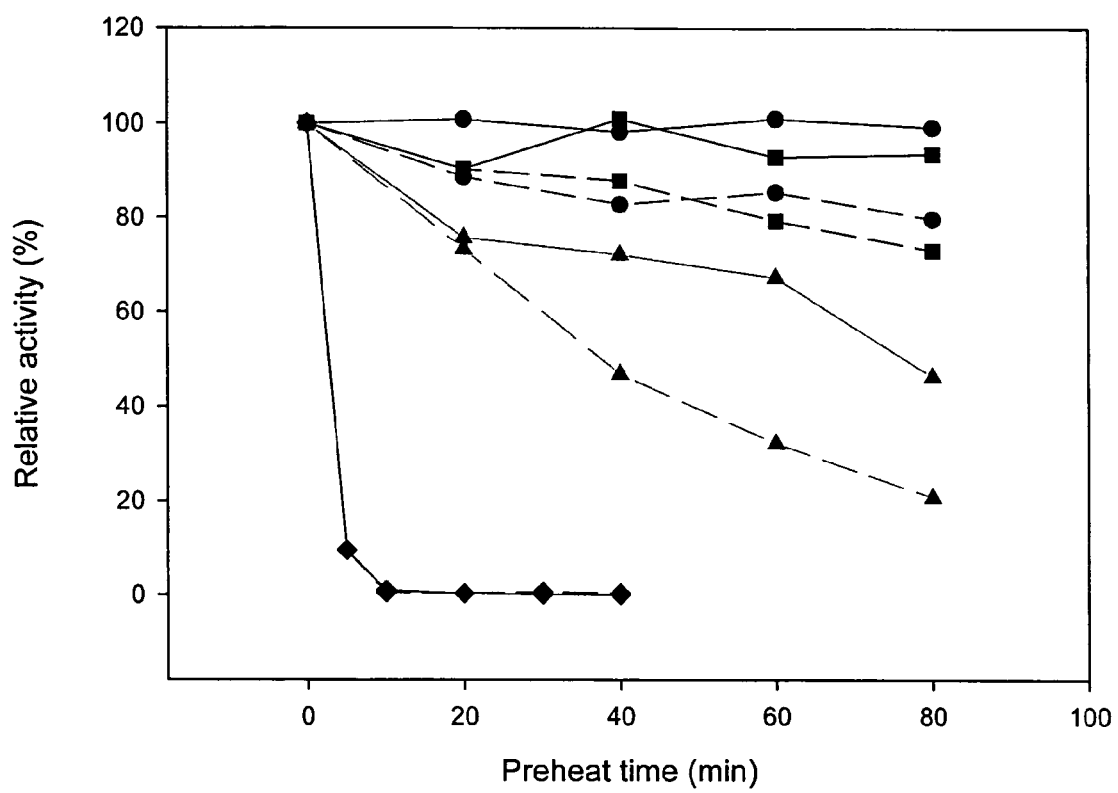
FIG. 4 is a broken line graph of heat stabilities of recombinant prolyl oligopeptidase wherein solid lines represent the pProHN14 protein, dotted lines represent the pProHN17 protein and shapes represent a temperature of preheated treatment, respectively being: circles representing 30° C., squares representing 37° C., triangles representing 45° C. and diamonds representing 55° C.

With reference to FIG. 4, being preheated at 30° C. or 37° C. for 80 minutes, the protein expressed from pProHN14 was observed to retain 99% and 93% of activities. The protein expressed from pProHN17 was observed to retain 80% and 73% of activities under the same conditions.

Being preheated at 45° C. for 60 minutes, the protein of pProHN14 was observed to retain 67% of activity. The protein of pProHN17 was observed to retain 32% of activity. Thus it was apparent that the protein of pProHN14 has better heat stability than the protein of pProHN17.

Being preheated at 55° C. for 5 minutes, the proteins of pProHN14 and pProHN17 were both observed to retain only 9% activities.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An isolated protein selected from the group consisting of:
   (a) a protein comprising the amino acid sequence of SEQ ID NO:6;
   (b) a protein encoded by a nucleic acid comprising the sequence of SEQ ID NO:5, wherein said protein has prolyl oligopeptidase activity.

2. A pharmaceutical composition for treating celiac disease caused by proline abundant gluten comprising administrating a pharmaceutical acceptable amount of the protein of claim 1 and a pharmaceutically acceptable excipient.

3. A composition for use with a proline-containing prodrug, comprising at least one pharmaceutically acceptable excipient and the protein of claim 1 wherein said protein is a functional component in said composition for converting said prodrug to a functional drug.

4. The composition of claim 3 further comprising an antibody.

* * * * *